United States Patent
Pinori et al.

(10) Patent No.: US 7,635,788 B2
(45) Date of Patent: Dec. 22, 2009

(54) ALPHA-AMINO ACID DERIVATIVES WITH ANTIINFLAMMATORY ACTIVITY

(75) Inventors: Massimo Pinori, Paderno d'Adda (IT); Rocco Mazzaferro, Milan (IT); Paolo Mascagni, Villasanta (IT)

(73) Assignee: Italfarmaco SpA, Milan (IT)

( * ) Notice: Subject to any disclaimer, the term of this patent is extended or adjusted under 35 U.S.C. 154(b) by 178 days.

(21) Appl. No.: 11/631,645

(22) PCT Filed: Jun. 7, 2005

(86) PCT No.: PCT/EP2005/052597

§ 371 (c)(1),
(2), (4) Date: Mar. 2, 2007

(87) PCT Pub. No.: WO2006/003068

PCT Pub. Date: Jan. 12, 2006

(65) Prior Publication Data

US 2008/0076807 A1    Mar. 27, 2008

(30) Foreign Application Priority Data

Jul. 5, 2004    (IT)    ............ MI2004A1347

(51) Int. Cl.
*C07C 259/10* (2006.01)
*A61K 31/19* (2006.01)

(52) U.S. Cl. .............. 562/622; 514/355; 514/464; 514/575; 546/316; 549/436

(58) Field of Classification Search .......... 562/622; 546/316; 549/436; 514/355, 464, 575
See application file for complete search history.

(56) References Cited

U.S. PATENT DOCUMENTS

| 6,034,096 A | 3/2000 | Bertolini et al. |
| 7,420,089 B2 * | 9/2008 | Verner et al. ............ 562/622 |

FOREIGN PATENT DOCUMENTS

WO    WO 02/26696 A1    4/2002

* cited by examiner

*Primary Examiner*—Shailendra Kumar
(74) *Attorney, Agent, or Firm*—Nixon & Vanderhye

(57) ABSTRACT

Compounds of the formula:

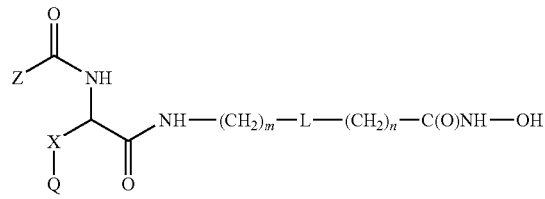

(I)

are described in which Z, Q, X, L, m and n assume the meanings stated in the description. The compounds (I) inhibit the production of TNF α and may thus be useful in the treatment of inflammation and pathological conditions involving overproduction of said cytokine. They furthermore exhibit significant inhibitory activity on the proliferation of tumour cells and may thus be used for the treatment and/or prevention of tumorous, neurodegenerative or autoimmune disorders.

9 Claims, No Drawings

ALPHA-AMINO ACID DERIVATIVES WITH ANTIINFLAMMATORY ACTIVITY

This application is the U.S. National Phase of International Application PCT/EP2005/052597 filed 7 Jun. 2005, which designated the U.S. PCT/2005/052597 claims priority to Italian Application No. MI2004A001347 filed 5 Jul. 2004. The entire content of these applications are incorporated herein by reference.

FIELD OF THE INVENTION

The present invention relates to alpha-amino acid derivatives, in particular derivatives containing an N-hydroxyamide function, having antiinflammatory activity and to the pharmaceutical compositions thereof.

BACKGROUND OF THE INVENTION

The role played by cytokines, in particular by interleukin 1β (IL1-β) and tumour necrosis factor α (TNF-α) in the development of the inflammatory response is well documented (Dinarello C. A. and Wolff S. M., *New Eng. J. Med.* 328(2): 106113, 1993; Tracey K. J. and Cerami A., *Crit. Care Med.* 21: S415, 1993; Melli M. and Parente L., *Cytokines and lipocortines in inflammation and differentiation*, Wiley-Liss. New York 1990; Dawson M. M. *Lymphokines and Interleukins. CRC Press. Boca Raton, Fla.* 1991). Research directed towards finding substances capable of inhibiting the production of cytokines has led to the development of cytokine suppressive antiinflammatory drugs (CSAID), among which are included so-called non-traditional nonsteroidal antiinflammatory drugs (Chiu G. C. Y. and Liou S. X. L, *Exp. Opin. Ther. Patents*, 6(1): 41, 1996). In some of these compounds, the presence of the hydroxylamine group appears to play a fundamental role in determining antiinflammatory activity (Tanaka et al., *Chem. Pharm. Bull.*, 31(8) 2810-2819, 1983).

EP901465 describes derivatives of hydroxamic acid containing an amidobenzoic moiety, which are capable of inhibiting the production of TNF-α and which have antiinflammatory and immunosuppressive activity; said compounds have furthermore demonstrated antitumour activity, as described in EP0208151.

DESCRIPTION OF THE INVENTION

It has now been found that hydroxamic acid derivatives containing an alpha-aminoacyl moiety have an inhibitory action on the production of proinflammatory cytokines, in particular of TNFα.

The present invention provides compounds of the formula (I)

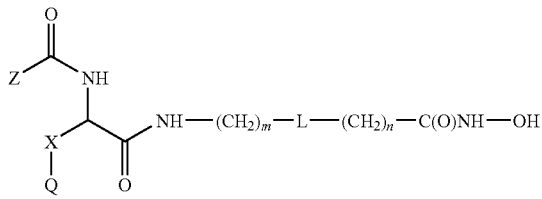

(I)

in which

Z is linear or branched $C_1$-$C_4$ alkyl, aryl, arylalkyl or a saturated, unsaturated or partially unsaturated mono-, di- or tricyclic carbocyclic residue, or a saturated, unsaturated or partially unsaturated mono-, di- or tricyclic heterocyclic residue comprising one or more heteroatoms selected from among N, S or O;

said $C_1$-$C_4$ alkyl, aryl, arylalkyl, carbocyclic or heterocyclic residue optionally being substituted with one or more mutually identical or different residues, selected from among: halogen, lower alkyl, lower alkoxyl, lower haloalkyl, alkylsulfonyl, cycloalkyl, (cycloalkyl)alkyl, alkanoyl, amino optionally mono- or disubstituted with $C_1$-$C_4$ alkyl, ($C_1$-$C_4$) aminoalkyl, optionally mono- or disubstituted with $C_1$-$C_4$ alkyl, carboxy, $C_1$-$C_4$ alkoxycarbonyl, mercaptoalkoxy, mercaptophenoxy, nitro, cyano, oxo, perfluoroalkoxy, perfluoroalkyl, phenyl, phenoxy, phenylalkoxy, benzoyloxy, phenylalkyl, benzoyl, phenylsulfonyl and hydroxy;

Q is aryl, arylalkyl or a saturated, unsaturated or partially unsaturated mono-, di- or tricyclic carbocyclic residue, or a saturated, unsaturated or partially unsaturated mono-, di- or tricyclic heterocyclic residue comprising one or more heteroatoms selected from among N, S or O;

said aryl, arylalkyl, carbocyclic or heterocyclic residue optionally being substituted with one or more mutually identical or different residues, selected from among: halogen, lower alkyl, lower alkoxyl, lower haloalkyl, alkylsulfonyl, cycloalkyl, (cycloalkyl)alkyl, alkanoyl, amino optionally mono- or disubstituted with $C_1$-$C_4$ alkyl, ($C_1$-$C_4$) aminoalkyl, optionally mono- or disubstituted with $C_1$-$C_4$ alkyl, carboxy, $C_1$-$C_4$ alkoxycarbonyl, mercaptoalkoxy, mercaptophenoxy, nitro, cyano, oxo, perfluoroalkoxy, perfluoroalkyl, phenyl, phenoxy, phenylalkoxy, benzoyloxy, phenylalkyl, benzoyl, phenylsulfonyl and hydroxy;

m and n are independently 0 or 1;

X is $C_1$-$C_4$ alkylene or is absent;

L is phenylene, cyclohexylene or a linear or branched alkyl chain with 2 to 6 carbon atoms, optionally containing one or more double bonds; and the pharmaceutically acceptable salts thereof.

The compounds of the invention contain one or more chiral centres (asymmetric carbon atoms) and may thus exist in enantiomeric and/or diastereoisomeric forms; all possible optical isomers, alone or mixed with one another, fall within the scope of the present invention.

Pharmaceutically acceptable salts of compounds of the formula I are those with organic and inorganic acids, such as for example, hydrochloric, hydrobromic, hydroiodic, nitric, sulfuric, phosphoric, acetic, benzoic, maleic, fumaric, succinic, tartaric, citric, aspartic, methanesulfonic acid or with inorganic bases such as, for example, sodium or potassium salts or with organic bases such as, for example, lysine, arginine or other amino acids or amines.

One class of preferred compounds comprises compounds of the formula I in which L is 1,4-phenylene, n and m are 0 and X is methylene or is absent. Another class of preferred compounds comprises compounds of the formula I in which Z is selected from among methyl, phenyl, naphthyl, benzo[1,3] dioxolyl and pyridyl, optionally substituted as stated above. Another class of preferred compounds comprises compounds of the formula I in which Q is selected from among naphthyl, indanyl, phenyl and biphenyl, optionally substituted as specified above.

One class of more preferred compounds comprises compounds of the formula I in which L is 1,4-phenylene, n and m are 0, X is methylene or is absent and Q represents a carbocycle selected from among naphthyl, indanyl, phenyl and biphenyl, optionally substituted as specified above.

Another class of more preferred compounds comprises compounds of the formula I in which L is 1,4-phenylene, n and m are 0, X is methylene or is absent and Z is selected from among $C_1$-$C_3$ alkyl, phenyl, naphthyl, pyridyl and benzo[1,3]dioxolyl.

One class of still more preferred compounds comprises compounds of the formula I in which L is 1,4-phenylene, n and m are 0, X is methylene or is absent, Q represents a carbocycle selected from among naphthyl, indanyl and phenyl and Z is selected from among $C_1$-$C_3$ alkyl, phenyl, naphthyl, pyridyl and benzo[1,3]dioxolyl.

The following compounds of the formula I are particularly preferred:

a) 4-(2(R)-Benzoylamino-3-naphthalen-2-yl-propionylamino)-N-hydroxy-benzamide b) 4-(2(R)-Acetylamino-3-naphthalen-2-yl-propionylamino)-N-hydroxy-benzamide c) 4-(2(S)-Acetylamino-2-indan-2-yl-acetylamino)-N-hydroxy-benzamide d) 4-(2(S)-Acetylamino-3-naphthalen-2-yl-propionylamino)-N-hydroxy-benzamide e) 4-(2(S)-Acetylamino-3-phenyl-propionylamino)-N-hydroxy-benzamide f) 4-(2(S)-Benzoylamino-3-biphenyl-4-yl-propionylamino)-N-hydroxy-benzamide g) 4-(2(S)-Benzoylamino-3-naphthalen-2-yl-propionylamino)-N-hydroxy-benzamide h) 4-(2(S)-Benzoylamino-3-phenyl-propionylamino)-N-hydroxy-benzamide i) 4-[2(S)-Acetylamino-3-(4-hydroxy-phenyl)-propionylamino]-N-hydroxy-benzamide j) 4-[2(S)-Acetylamino-3-(4-trifluoromethyl-phenyl)-propionylamino]-N-hydroxy-benzamide k) 4-[2(S)-Benzoylamino-3-(4-hydroxy-phenyl)-propionylamino]-N-hydroxy-benzamide l) 4-Amino-N-[1(R)-(4-hydroxycarbamoyl-phenylcarbamoyl)-2-naphthalen-2-yl-ethyl]-benzamide m) 4-Amino-N-[1(S)-(4-hydroxycarbamoyl-phenylcarbamoyl)-2-naphthalen-2-yl-ethyl]-benzamide n) 5-Bromo-N-[1(R)-(4-hydroxycarbamoyl-phenylcarbamoyl)-2-naphthalen-2-yl-ethyl]-nicotinamide o) 5-Bromo-N-[1(S)-(4-hydroxycarbamoyl-phenylcarbamoyl)-2-(4-trifluoromethyl-phenyl)-ethyl]-nicotinamide p) 5-Bromo-N-[1(S)-(4-hydroxycarbamoyl-phenylcarbamoyl)-2-biphenyl-4-yl-ethyl]-nicotinamide q) 5-Bromo-N-[1(S)-(4-hydroxycarbamoyl-phenylcarbamoyl)-2-naphthalen-2-yl-ethyl]-nicotinamide r) N-[1(R)-(4-hydroxycarbamoyl-phenylcarbamoyl)-2-naphthalen-2-yl-ethyl]-amide of benzo[1,3]dioxole-5-carboxylic acid s) N-[1(S)-(4-hydroxycarbamoyl-phenylcarbamoyl)-2-(4-hydroxy-phenyl)-ethyl]-amide of benzo[1,3]dioxole-5-carboxylic acid t) N-[1(S)-(4-hydroxycarbamoyl-phenylcarbamoyl)-2-naphthalen-2-yl-ethyl]-amide of benzo[1,3]dioxole-5-carboxylic acid u) N-[1(S)-(4-hydroxycarbamoyl-phenylcarbamoyl)-2-(3-fluoro-phenyl)-ethyl]-amide of benzo[1,3]dioxole-5-carboxylic acid v) N-[1(R)-(4-hydroxycarbamoyl-phenylcarbamoyl)-2-naphthalen-2-yl-ethyl]-amide of naphthalene-2-carboxylic acid w) N-[1(S)-(4-hydroxycarbamoyl-phenylcarbamoyl)-2-(4-trifluoromethyl-phenyl)-ethyl]-amide of naphthalene-2-carboxylic acid x) N-[1(S)-(4-hydroxycarbamoyl-phenylcarbamoyl)-2-phenyl-ethyl]-amide of naphthalene-2-carboxylic acid y) N-[1(S)-(4-hydroxycarbamoyl-phenylcarbamoyl)-2-(biphenyl-4-yl)-ethyl]-amide of naphthalene-2-carboxylic acid The compounds of the invention may be prepared using methods known to the person skilled in the art; for example, they may be prepared by means of "solid phase" organic synthesis using one of the special commercially available resins for N-hydroxyamides. A polystyrene resin crosslinked with divinylbenzene and functionalised with O-alkylated hydroxylamine groups from para-alkoxybenzyl residues (Wang resins) may be used for this purpose [c.f. for example Richter, L. S, and Desai, M. C. *Tetrahedron Letters* 38(3) pp. 321-322 (1996)].

The amino groups present on the resin may be acylated, in presence of appropriate condensing agents, with protected intermediates of the formula

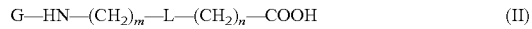

$$G-HN-(CH_2)_m-L-(CH_2)_n-COOH \quad (II)$$

in which L, m and n have the same meanings specified above and G is a suitable protective group.

A resin of the formula

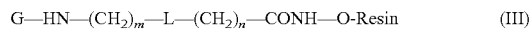

$$G-HN-(CH_2)_m-L-(CH_2)_n-CONH-O\text{-Resin} \quad (III)$$

will be obtained, the amino group of which, after removal of the protective group G, may subsequently be acylated using an α-amino acid derivative of the formula,

(IV)

in which Q, X and G have the meanings specified above; after subsequent removal of the protective group G, the liberated amino group may be definitively acylated using acids of the formula,

$$Z-C(O)OH \quad (V)$$

where Z has the meanings specified above, either in activated form (for example acyl chlorides, active esters, etc.), or in the presence of condensing agents.

The products of the invention may finally be liberated from the resin by treatment with medium-strength acids, for example trifluoroacetic acid, filtration and optional final purification.

Salts of the compounds of the formula I are prepared using known methods. The compounds of the invention, used at concentrations of between 1 and 1000 nM, preferably between 1 and 200 nM, bring about a 50% inhibition in the production of TNFα by peripheral blood mononucleocytes stimulated with LPS according to the test described by R. de Waal Malefy, et al. (*J. Exp. Med.*, 1991, 174: 1209-1220) and may thus be used as medicines, in particular as medicines for the treatment of disorders or pathological conditions involving overproduction of TNFα or of proinflammatory cytokines.

The compounds of the formula I furthermore exhibit significant activity in in vitro cytotoxicity testing on human hepatoma cell line Hep-G2, as described, for example in Example 4, this test being predictive of in vivo antitumour activity. These compounds may accordingly be used, alone or together with other antitumour drugs, not only in the treatment of tumorous disorders, but also for the treatment of neurodegenerative or autoimmune diseases.

The present invention accordingly also provides pharmaceutical compositions comprising a therapeutically effective quantity of the compounds of the formula (I) or of the pharmaceutically acceptable salts thereof together with at least one pharmaceutically acceptable excipient and/or carrier, such as for example those described in Remington's Pharmaceutical Sciences Handbook, XVII edition, Mack Pub., NY, USA. Such compositions may be liquid, suitable for enteral or parenteral administration, or solid, for example, in the form of capsules, tablets, coated tablets, powders or granules for oral administration, or in forms suitable for cutaneous administration, such as for example creams or ointments, or inhalatory administration.

The pharmaceutical compositions provided by the present invention may be prepared using known methods.

The present invention will be illustrated below with reference to some Examples which should not be viewed as in any way limiting the scope of the invention.

EXAMPLES

The abbreviations below are used in the following Examples:

ACN acetonitrile
PVDF polyvinylidene difluoride
DCM dichloromethane
DIPEA diisopropylethylamine
DMF dimethylformamide
HOAt 1-hydroxy-7-azabenzotriazole
HATU O-(7-azabenzotriazol-1-yl)-N,N,N'N'-tetramethyluronium hexafluorophosphate
TFA trifluoroacetic acid General Purification Method Unless stated otherwise, all final purifications were performed by means of a Waters preparative HPLC/MS system with a Waters Symmetry C18 5 mm 19×50 mm column, fitted to a Waters ZQ mass spectrometer.

Operating Conditions:

Centroid ES$^+$ ionisation, scan time 15 min, m/z scan 120-1000, cone voltage 15 V, source temperature 120° C., solvation temperature 250° C.

HPLC Eluents:

A=$H_2O$, B=ACN, C=1% HCOOH in $H_2O$

Gradient:

| Time (min) | A | B | C | Flow rate (ml/min) |
| --- | --- | --- | --- | --- |
| 0 | 94% | 5% | 1% | 20 |
| 2 | 94% | 5% | 1% | 20 |
| 3 | 87% | 12% | 1% | 20 |
| 8 | 87% | 12% | 1% | 20 |
| 11 | 20% | 80% | 1% | 20 |
| 12 | 94% | 5% | 1% | 20 |

An aliquot of the crude product to be purified (30-50 mg) was dissolved in 0.1 ml of MeOH and diluted with 0.4 ml of ACN/$H_2O$ mixture (1:1; vol./vol.). The solution, filtered through a 0.45 mm PVDF membrane, was injected into the above-described preparative system. For each run, the fractions corresponding to the peak associated with the expected molecular ion ([M+H]$^+$) were collected, combined and concentrated to dryness.

Example 1 a) 4-(2(R)-Benzoylamino-3-naphthalen-2-yl-propionylamino)-N-hydroxy-benzamide

Step A

A mixture of HOAt (5.1 g; 37.5 mmol) and HATU (14.3 g; 37.5 mmol) in anhydrous DMF (20 ml) was added to a solution of 4-(9H-fluoren-9-yl-methoxycarbonylamino)-benzoic acid (13.5 g; 37.5 mmol) in anhydrous DMF (25 ml) and diisopropylethylamine (13 ml; 75 mmol) was then added. The reaction mixture was stirred at ambient temperature for 30 minutes, then was transferred into a reactor containing a Wang type polystyrene resin functionalised with hydroxylamine (9 g; 9.36 mmol) and the suspension was stirred at ambient temperature for 16 hours. The resin was filtered out and washed, in succession, with DMF (5×50 ml), DCM (4×50 ml), MeOH (3×50 ml) and DCM (5×50 ml), was finally filtered out and dried under a vacuum.

Step B

An aliquot of the resin obtained in A (150 mg) was transferred into a solid phase synthesis reactor and reswollen with a 20% solution of piperidine in DMF (2 ml). After having been stirred at ambient temperature for one hour, the resin was filtered out and washed with DMF (5×2 ml).

Step C

HATU (237 mg, 0.62 mmol), HOAt (85 mg; 0.62 mmol) and DIPEA (0.217 ml; 1.24 mmol) were added to a solution of (9H-fluoren-9-yl)-methoxycarbonyl-D-(2)naphthylalanine (Fmoc-D(2)NaI-OH; 273 mg, 0.62 mmol) in DMF (1.5 ml). The solution (~2 ml) was added to the reactor containing the resin obtained in B and stirred overnight at ambient temperature. The resin was filtered out and washed, in succession, with DMF (5×2 ml), DCM (2×2 ml), MeOH (2×2 ml), DCM (2×2 ml) and finally filtered out under a vacuum.

Step D

The resin obtained in C was treated with 20% piperidine in DMF, as described in step B.

Step E

HATU (237 mg, 0.62 mmol), HOAt (85 mg; 0.62 mmol) and DIPEA (0.217 ml; 1.24 mmol) were added to a solution of benzoic acid (76 mg; 0.62 mmol) in DMF (1.5 ml). The solution (~2 ml) was added to the reactor containing the resin obtained in D and stirred overnight at ambient temperature. The resin was filtered out and washed, in succession, with DMF (5×2 ml), DCM (2×2 ml), MeOH (2×2 ml), DCM (2×2 ml) and finally filtered out under a vacuum.

Step F

The resin obtained as described in the preceding point was reswollen in a 50% solution of TFA in DCM (2 ml) and stirred at ambient temperature for one hour, then was filtered out and the solution was evaporated to dryness. The residue was resuspended with t-BuOMe and evaporated five more times. The residue obtained was purified by means of preparative HPLC/MS in accordance with the previously described general method.

Product obtained: 16.9 mg; $[M+H]^+$=454.3 (calc. 454.2)

Example 2

The following products were prepared using the procedure described in Example 1:

b)  4-(2(R)-Acetylamino-3-naphthalen-2-yl-propionylamino)-N-hydroxy-benzamide
c)  4-(2(S)-Acetylamino-2-indan-2-yl-acetylamino)-N-hydroxy-benzamide
d)  4-(2(S)-Acetylamino-3-naphthalen-2-yl-propionylamino)-N-hydroxy-benzamide
e)  4-(2(S)-Acetylamino-3-phenyl-propionylamino)-N-hydroxy-benzamide
f)  4-(2(S)-Benzoylamino-3-biphenyl-4-yl-propionylamino)-N-hydroxy-benzamide
g)  4-(2(S)-Benzoylamino-3-naphthalen-2-yl-propionylamino)-N-hydroxy-benzamide
h)  4-(2(S)-Benzoylamino-3-phenyl-propionylamino)-N-hydroxy-benzamide
i)  4-[2(S)-Acetylamino-3-(4-hydroxy-phenyl)-propionylamino]-N-hydroxy-benzamide
j)  4-[2(S)-Acetylamino-3-(4-trifluoromethyl-phenyl)-propionylamino]-N-hydroxy-benzamide
k)  4-[2(S)-Benzoylamino-3-(4-hydroxy-phenyl)-propionylamino]-N-hydroxy-benzamide
l)  4-Amino-N-[1(R)-(4-hydroxycarbamoyl-phenylcarbamoyl)-2-naphthalen-2-yl-ethyl]-benzamide
m)  4-Amino-N-[1(S)-(4-hydroxycarbamoyl-phenylcarbamoyl)-2-naphthalen-2-yl-ethyl]-benzamide
n)  5-Bromo-N-[1(R)-(4-hydroxycarbamoyl-phenylcarbamoyl)-2-naphthalen-2-yl-ethyl]-nicotinamide
o)  5-Bromo-N-[1(S)-(4-hydroxycarbamoyl-phenylcarbamoyl)-2-(4-trifluoromethyl-phenyl)-ethyl]-nicotinamide
p)  5-Bromo-N-[1(S)-(4-hydroxycarbamoyl-phenylcarbamoyl)-2-biphenyl-4-yl-ethyl]-nicotinamide
q)  5-Bromo-N-[1(S)-(4-hydroxycarbamoyl-phenylcarbamoyl)-2-naphthalen-2-yl-ethyl]-nicotinamide
r)  N-[1(R)-(4-hydroxycarbamoyl-phenylcarbamoyl)-2-naphthalen-2-yl-ethyl]-amide of benzo[1,3]dioxole-5-carboxylic acid
s)  N-[1(S)-(4-hydroxycarbamoyl-phenylcarbamoyl)-2-(4-hydroxy-phenyl)-ethyl]-amide of benzo[1,3]dioxole-5-carboxylic acid
t)  N-[1(S)-(4-hydroxycarbamoyl-phenylcarbamoyl)-2-naphthalen-2-yl-ethyl]-amide of benzo[1,3]dioxole-5-carboxylic acid
u)  N-[1(S)-(4-hydroxycarbamoyl-phenylcarbamoyl)-2-(3-fluoro-phenyl)-ethyl]-amide of benzo[1,3]dioxole-5-carboxylic acid
v)  N-[1(R)-(4-hydroxycarbamoyl-phenylcarbamoyl)-2-naphthalen-2-yl-ethyl]-amide of naphthalene-2-carboxylic acid
w)  N-[1(S)-(4-hydroxycarbamoyl-phenylcarbamoyl)-2-(4-trifluoromethyl-phenyl)-ethyl]-amide of naphthalene-2-carboxylic acid
x)  N-[1(S)-(4-hydroxycarbamoyl-phenylcarbamoyl)-2-phenyl-ethyl]-amide of naphthalene-2-carboxylic acid
y)  N-[1(S)-(4-hydroxycarbamoyl-phenylcarbamoyl)-2-(biphenyl-4-yl)-ethyl]-amide of naphthalene-2-carboxylic acid Example 3

Inhibition of the Production of TNFα

In Vitro Determination

The compounds were dissolved in DMSO at a final concentration of 10 mM.

The solutions for the assay were prepared by diluting the mother solutions in RPMI 1640 with the addition of 1% FCS and 0.01% DMSO and were filtered with 0.2 µm filters.

The peripheral blood mononucleocytes were obtained from blood from healthy donors by separation in a Ficoll-Hypaque gradient [C. G. Figdor, et al. *Blood,* 1982, 60: 46-53]. The cells were sown in 96-well plates, at a concentration of approx. 500,000 cells per well, suspended in RPMI 1640 containing 1% FCS and were incubated at 37° C. in the presence of different concentrations (from $10^{-6}$ to $10^{-11}$M) of the compounds to be investigated. After 1 hour, LPS was added (at a final concentration of 10 ng/ml; obtained from *E. coli* 055:B5) and the plates were incubated at 37° C. for a further 24 hours. At the end of this period, the supernatants were collected and used for the determination of TNFα content by means of ELISA (DuoSet ELISA kit; R&D Systems, Minneapolis, Minn., USA).

The concentration of TNFα was calculated using a calibration curve and the $IC_{50}$ values (the concentration which brings about 50% inhibition of the production of the cytokine) were calculated from the curve obtained by plotting the percentage inhibition values for each individual concentration of the compound under investigation.

TABLE 1

| Inhibition of TNFα production by human monocytes stimulated with LPS | |
|---|---|
| Example | $IC_{50}$ (nM) |
| 1a | 3.0 |
| 2b | 51.8 |
| 2c | 55.9 |
| 2d | 4.4 |
| 2e | 12.5 |
| 2f | 72.1 |
| 2g | 6.1 |
| 2h | 11.3 |
| 2i | 13.3 |
| 2j | 4.6 |
| 2k | 148.4 |
| 2l | 29.6 |
| 2m | 26.7 |
| 2n | 6.8 |
| 2o | 200.0 |
| 2p | 42.0 |

TABLE 1-continued

Inhibition of TNFα production by
human monocytes stimulated with LPS

| Example | IC$_{50}$ (nM) |
|---------|----------------|
| 2q      | 22.9           |
| 2r      | 1.7            |
| 2s      | 1000.0         |
| 2t      | 4.8            |
| 2u      | 6.8            |
| 2v      | 16.8           |
| 2w      | 23.7           |
| 2x      | 8.6            |
| 2y      | 21.3           |

Example 4

Cytotoxicity Towards Tumour Cells In Vitro

The cytotoxicity of some compounds described in the preceding Examples was evaluated in vitro on human hepatoma cell line Hep-G2, by means of a commercial colorimetric method (Cell Titer 96® Aque ous One Solution Cell Proliferation Assay—Promega); the method determines the number of viable cells on the basis of their capacity to metabolise a tetrazolium salt producing formazane. The quantity of formazane produced is proportional to the number of viable cells.

The Hep-G2 cells are distributed 96 well microplates at a density of $4\times10^4$ cells/well (100 μl), in M199 medium containing 10% foetal bovine serum and supplements (complete medium).

After 24 hours' incubation (37° C., 5% CO$_2$, 90% humidity), the cells are washed once and the medium is replenished with 200 μl of complete medium containing the substances to be tested at the final concentration of $10^{-5}$, $10^{-6}$ and $10^{-7}$M. The test is performed in triplicate.

The plates are incubated for a further 48 h, at the end of which 100 μl of medium are removed and 20 μl/well of staining solution are added in accordance with the supplier's instructions. Optical density (λ=490 nm) is read after 1 hour's incubation at 37° C. using a plate reader (Victor2—Wallac Perkin Elmer).

The results, which demonstrate the antitumour activity of the class of compounds of the formula I, are stated as percentage inhibition of the formation of formazane relative to the control. The following Table shows the values obtained at the concentrations $10^{-5}$ M and $10^{-6}$ M.

TABLE 2

Percentage cytotoxicity toward Hep-G2 cells

| Example | Cytotoxicity at $10^{-6}$ M | Cytotoxicity at $10^{-5}$ M |
|---------|------------------------------|------------------------------|
| 1a      | 22.6%                        | 75.2%                        |
| 2b      | 10.6%                        | 48.3%                        |
| 2c      | 28.5%                        | 78.3%                        |
| 2d      | 9.6%                         | 56.2%                        |
| 2e      | 13.3%                        | 17.1%                        |
| 2f      | 22.7%                        | 81.6%                        |
| 2g      | 43.2%                        | 76.5%                        |
| 2h      | 31.2%                        | 77.4%                        |
| 2i      | 15.7%                        | 12.2%                        |
| 2j      | 15.8%                        | 39.3%                        |
| 2k      | 27.7%                        | 54.4%                        |
| 2l      | 14.4%                        | 61.9%                        |

TABLE 2-continued

Percentage cytotoxicity toward Hep-G2 cells

| Example | Cytotoxicity at $10^{-6}$ M | Cytotoxicity at $10^{-5}$ M |
|---------|------------------------------|------------------------------|
| 2m      | 24.5%                        | 72.4%                        |
| 2n      | 15.9%                        | 68.2%                        |
| 2o      | 34.8%                        | 72.4%                        |
| 2p      | 10.5%                        | 61.7%                        |
| 2q      | 11.7%                        | 53.9%                        |
| 2r      | 16.6%                        | 72.5%                        |
| 2t      | 48.5%                        | 79.3%                        |
| 2u      | 12.9%                        | 62.9%                        |
| 2v      | 11.8%                        | 69.4%                        |
| 2w      | 25.3%                        | 65.7%                        |
| 2x      | 15.3%                        | 77.3%                        |
| 2y      | 20.4%                        | 73.7%                        |

The invention claimed is:

1. A compound of the formula (I)

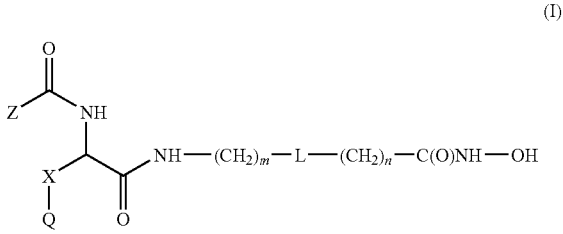

in which

Z is linear or branched $C_1$-$C_4$ alkyl, aryl, arylalkyl or a saturated, unsaturated or partially unsaturated mono-, di- or tricyclic carbocyclic residue, or a saturated, unsaturated or partially unsaturated mono-, di- or tricyclic heterocyclic residue comprising one or more heteroatoms selected from among N, S or O, said $C_1$-$C_4$ alkyl, aryl, arylalkyl, carbocyclic or heterocyclic residue optionally being substituted with one or more mutually identical or different residues, selected from among: halogen, lower alkyl, lower alkoxyl, lower haloalkyl, alkylsulfonyl, cycloalkyl, (cycloalkyl)alkyl, alkanoyl, amino optionally mono- or disubstituted with $C_1$-$C_4$ alkyl, ($C_1$-$C_4$) aminoalkyl, optionally mono- or disubstituted with $C_1$-$C_4$ alkyl, carboxy, $C_1$-$C_4$ alkoxycarbonyl, mercaptoalkoxy, mercaptophenoxy, nitro, cyano, oxo, perfluoroalkoxy, perfluoroalkyl, phenyl, phenoxy, phenylalkoxy, benzoyloxy, phenylalkyl, benzoyl, phenylsulfonyl and hydroxy;

Q is aryl, arylalkyl or a saturated, unsaturated or partially unsaturated mono-, di- or tricyclic carbocyclic residue, or a saturated, unsaturated or partially unsaturated mono-, di- or tricyclic heterocyclic residue comprising one or more heteroatoms selected from among N, S or O;

said aryl, arylalkyl, carbocyclic or heterocyclic residue optionally being substituted with one or more mutually identical or different residues, selected from among: halogen, lower alkyl, lower alkoxyl, lower haloalkyl, alkylsulfonyl, cycloalkyl, (cycloalkyl)alkyl, alkanoyl, amino optionally mono- or disubstituted with $C_1$-$C_4$ alkyl, ($C_1$-$C_4$) aminoalkyl, optionally mono- or disubstituted with $C_1$-$C_4$ alkyl, carboxy, $C_1$-$C_4$ alkoxycarbonyl, mercaptoalkoxy, mercaptophenoxy, nitro, cyano, oxo, perfluoroalkoxy, perfluoroalkyl, phenyl, phenoxy, phenylalkoxy, benzoyloxy, phenylalkyl, benzoyl, phenylsulfonyl and hydroxy;

m and n are independently 0 or 1;

X is $C_1$-$C_4$alkylene or is absent;

L is phenylene, cyclohexylene or a linear or branched alkyl chain with 2 to 6 carbon atoms, optionally containing one or more double bonds;

with the proviso that when Q is indole, L is 1,4-phenylene, m is 0 and n is 0: and the pharmaceutically acceptable salts thereof.

2. A compound according to claim 1, in which L is 1,4-phenylene, n and m are 0 and X is methylene or is absent.

3. A compound according to claim 1, in which Z is selected from among methyl, phenyl, naphthyl, benzo[1,3]dioxolyl and pyridyl, optionally substituted as stated in claim 1.

4. A compound according to claim 1, in which Q is selected from among naphthyl, indanyl, phenyl and biphenyl optionally substituted as stated in claim 1.

5. A compound according to claim 1, in which L is 1,4-phenylene, n and m are 0, X is methylene or is absent and Q represents a carbocycle selected from among naphthyl, indanyl, phenyl and biphenyl, optionally substituted as stated in claim 1.

6. A compound according to claim 1, in which L is 1,4-phenylene, n and m are 0, X is methylene or is absent and Z is selected from among $C_1$-$C_3$ alkyl, phenyl, naphthyl, pyridyl and benzo[1,3]dioxolyl, optionally substituted as stated in claim 1.

7. A compound according to claim 1, in which L is 1,4-phenylene, n and m are 0, X is methylene or is absent, Q represents a carbocycle selected from among naphthyl, indanyl, phenyl and biphenyl and Z is selected from among $C_1$-$C_3$ alkyl, phenyl, naphthyl, pyridyl and benzo[1,3]dioxolyl, optionally substituted as stated in claim 1.

8. A compound selected from among:

4-(2(R)-Benzoylamino-3-naphthalen-2-yl-propionylamino)-N-hydroxy-benzamide 4-(2(R)-Acetylamino-3-naphthalen-2-yl-propionylamino)-N-hydroxy-benzamide 4-(2(S)-Acetylamino-2-indan-2-yl-acetylamino)-N-hydroxy-benzamide 4-(2(S)-Acetylamino-3-naphthalen-2-yl-propionylamino)-N-hydroxy-benzamide 4-(2(S)-Acetylamino-3-phenyl-propionylamino)-N-hydroxy-benzamide 4-(2(S)-Benzoylamino-3-biphenyl-4-yl-propionylamino)-N-hydroxy-benzamide 4-(2(S)-Benzoylamino-3-naphthalen-2-yl-propionylamino)-N-hydroxy-benzamide 4-(2(S)-Benzoylamino-3-phenyl-propionylamino)-N-hydroxy-benzamide 4-[2(S)-Acetylamino-3-(4-hydroxy-phenyl)-propionylamino]-N-hydroxy-benzamide 4-[2(S)-Acetylamino-3-(4-trifluoromethyl-phenyl)-propionylamino]-N-hydroxy-benzamide 4-[2(S)-Benzoylamino-3-(4-hydroxy-phenyl)-propionylamino]-N-hydroxy-benzamide 4-Amino-N-[1(R)-(4-hydroxycarbamoyl-phenylcarbamoyl)-2-naphthalen-2-yl-ethyl]-benzamide 4-Amino-N-[1(S)-(4-hydroxycarbamoyl-phenylcarbamoyl)-2-naphthalen-2-yl-ethyl]-benzamide 5-Bromo-N-[1(R)-(4-hydroxycarbamoyl-phenylcarbamoyl)-2-naphthalen-2-yl-ethyl]-nicotinamide 5-Bromo-N-[1(S)-(4-hydroxycarbamoyl-phenylcarbamoyl)-2-(4-trifluoromethyl-phenyl)-ethyl]-nicotinamide 5-Bromo-N-[1(S)-(4-hydroxycarbamoyl-phenylcarbamoyl)-2-biphenyl-4-yl-ethyl]-nicotinamide 5-Bromo-N-[1(S)-(4-hydroxycarbamoyl-phenylcarbamoyl)-2-naphthalen-2-yl-ethyl]-nicotinamide N-[1(R)-(4-hydroxycarbamoyl-phenylcarbamoyl)-2-naphthalen-2-yl-ethyl)-amide of benzo[1,3]dioxole-5-carboxylic acid N-[1(S)-(4-hydroxycarbamoyl-phenylcarbamoyl)-2-(4-hydroxy-phenyl)-ethyl]-amide of benzo[1,3]dioxole-5-carboxylic acid N-[1(S)-(4-hydroxycarbamoyl-phenylcarbamoyl)-2-naphthalen-2-yl-ethyl]-amide of benzo[1,3]dioxole-5-carboxylic acid N-[1(S)-(4-hydroxycarbamoyl-phenylcarbamoyl)-2-(3-fluoro-phenyl)-ethyl]-amide of benzo[1,3]dioxole-5-carboxylic acid N-[1(R)-(4-hydroxycarbamoyl-phenylcarbamoyl)-2-naphthalen-2-yl-ethyl]-amide of naphthalene-2-carboxylic acid N-[1(S)-(4-hydroxycarbamoyl-phenylcarbamoyl)-2-(4-trifluoromethyl-phenyl)-ethyl]-amide of naphthalene-2-carboxylic acid N-[1(S)-(4-hydroxycarbamoyl-phenylcarbamoyl)-2-phenyl-ethyl]-amide of naphthalene-2-carboxylic acid N-[1(S)-(4-hydroxycarbamoyl-phenylcarbamoyl)-2-(biphenyl-4-yl)-ethyl]-amide of naphthalene-2-carboxylic acid.

9. A pharmaceutical composition comprising a therapeutically effective quantity of at least one compound of the formula (I) according to claim 1 or a pharmaceutically acceptable salt thereof together with at least one pharmaceutically acceptable excipient and/or carrier.

* * * * *